United States Patent
Kang et al.

(10) Patent No.: US 10,172,519 B2
(45) Date of Patent: *Jan. 8, 2019

(54) BIOSIGNAL TRANSMITTER, BIOSIGNAL RECEIVER, AND METHOD OF TRANSMITTING AND RECEIVING BIOSIGNAL

(71) Applicant: Samsung Electronics Co., Ltd., Suwon-si (KR)

(72) Inventors: Jae Min Kang, Seoul (KR); Kun Kook Park, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/221,994

(22) Filed: Jul. 28, 2016

(65) Prior Publication Data
US 2016/0331234 A1 Nov. 17, 2016

Related U.S. Application Data

(62) Division of application No. 14/056,705, filed on Oct. 17, 2013, now Pat. No. 9,427,157.

(30) Foreign Application Priority Data

Nov. 12, 2012 (KR) .......................... 10-2012-0127417

(51) Int. Cl.
*A61B 5/06* (2006.01)
*A61B 5/00* (2006.01)
(Continued)

(52) U.S. Cl.
CPC .......... *A61B 5/0006* (2013.01); *A61B 5/0408* (2013.01); *A61B 5/04017* (2013.01);
(Continued)

(58) Field of Classification Search
CPC ... A61B 5/0006; A61B 5/0456; A61B 5/0408; A61B 5/04525; A61B 5/7232; A61B 5/7264; G06K 9/0053
See application file for complete search history.

(56) References Cited

U.S. PATENT DOCUMENTS

| 4,531,527 A | 7/1985 | Reinhold, Jr. et al. |
| 4,567,883 A | 2/1986 | Langer et al. |

(Continued)

FOREIGN PATENT DOCUMENTS

| CN | 101272733 A | 9/2008 |
| CN | 101773392 A | 7/2010 |

(Continued)

OTHER PUBLICATIONS

Extended European Search Report dated Mar. 5, 2014 in counterpart European Patent Application No. 13186567.7. (7 pages in English).

(Continued)

*Primary Examiner* — Rex R Holmes
(74) *Attorney, Agent, or Firm* — NSIP Law

(57) ABSTRACT

Technology for transmitting and receiving a biosignal based on a pattern related to the biosignal and a feature point included in the biosignal. A biosignal transmitter includes a biosignal obtaining unit configured to obtain a biosignal comprising a plurality of unit signals, a parsing unit configured to parse the biosignal to extract a first unit signal of the plurality of unit signals, a pattern obtaining unit configured to obtain a pattern related to the biosignal based on the first unit signal, and a transmitting unit configured to transmit information related to a feature point of the first unit signal based on the first unit signal and the pattern.

9 Claims, 9 Drawing Sheets

(51) Int. Cl.
*A61B 5/0452* (2006.01)
*A61B 5/0408* (2006.01)
*A61B 5/0456* (2006.01)
*G06K 9/00* (2006.01)
*A61B 5/04* (2006.01)

(52) U.S. Cl.
CPC ........ *A61B 5/0456* (2013.01); *A61B 5/04525* (2013.01); *G06K 9/0053* (2013.01); *A61B 5/7232* (2013.01); *A61B 5/7264* (2013.01)

(56) References Cited

U.S. PATENT DOCUMENTS

| | | | |
|---|---|---|---|
| 4,583,553 A * | 4/1986 | Shah | A61B 5/04325 |
| | | | 600/517 |
| 5,273,049 A | 12/1993 | Steinhaus et al. | |
| 9,427,157 B2 * | 8/2016 | Kang | G06K 9/0053 |
| 2003/0120164 A1 | 6/2003 | Nielsen et al. | |
| 2008/0214946 A1 | 9/2008 | Miller | |
| 2012/0184858 A1 * | 7/2012 | Harlev | A61B 5/0402 |
| | | | 600/484 |
| 2014/0005988 A1 * | 1/2014 | Brockway | H03H 17/0248 |
| | | | 703/2 |

FOREIGN PATENT DOCUMENTS

| | | |
|---|---|---|
| CN | 101877035 A | 11/2010 |
| JP | 2001-198094 A | 7/2001 |
| JP | 2007-190131 A | 8/2007 |
| JP | 2007-523732 A | 8/2007 |
| JP | 2009-195447 A | 9/2009 |
| JP | 2010-51592 A | 3/2010 |
| KR | 10-2009-0089039 A | 8/2009 |
| KR | 10-2010-0067363 A | 6/2010 |
| KR | 10-2010-0067364 A | 6/2010 |
| KR | 10-2010-0076648 A | 7/2010 |
| KR | 10-2011-0011768 A | 2/2011 |

OTHER PUBLICATIONS

Chinese Office Action dated Mar. 7, 2016 in counterpart Chinese Application No. 201310473107.3. (18 pages in Chinese with English translation).

* cited by examiner

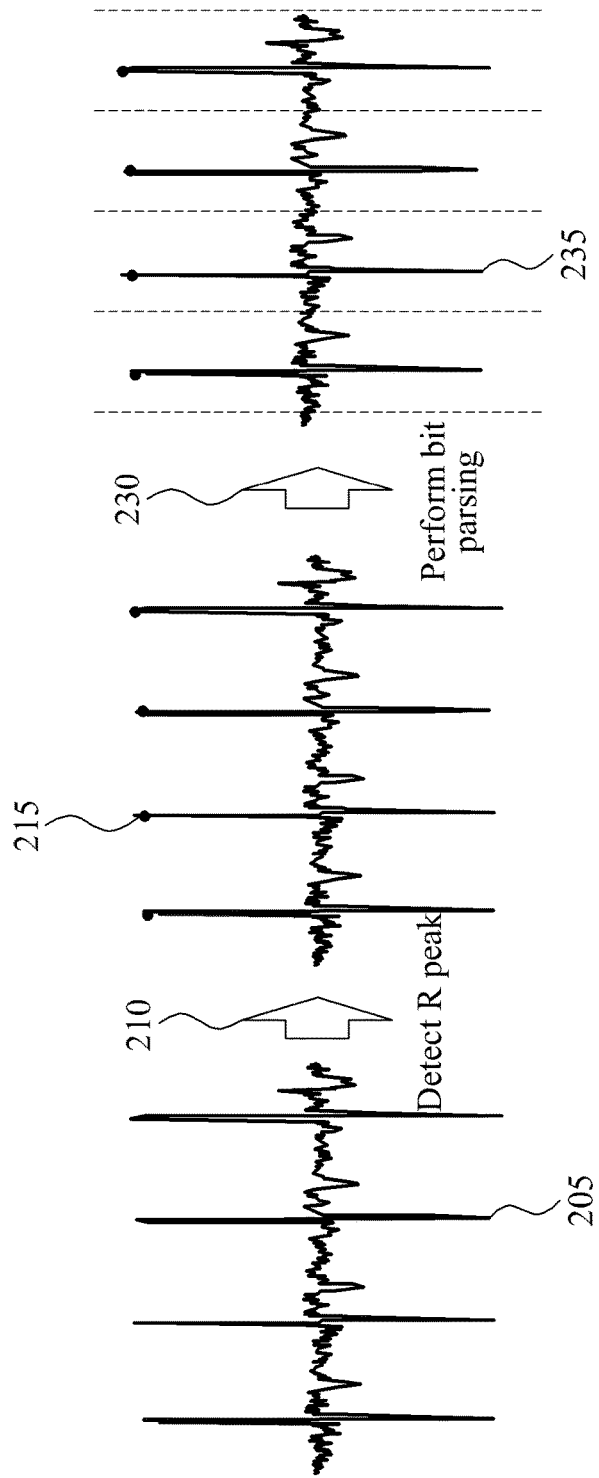

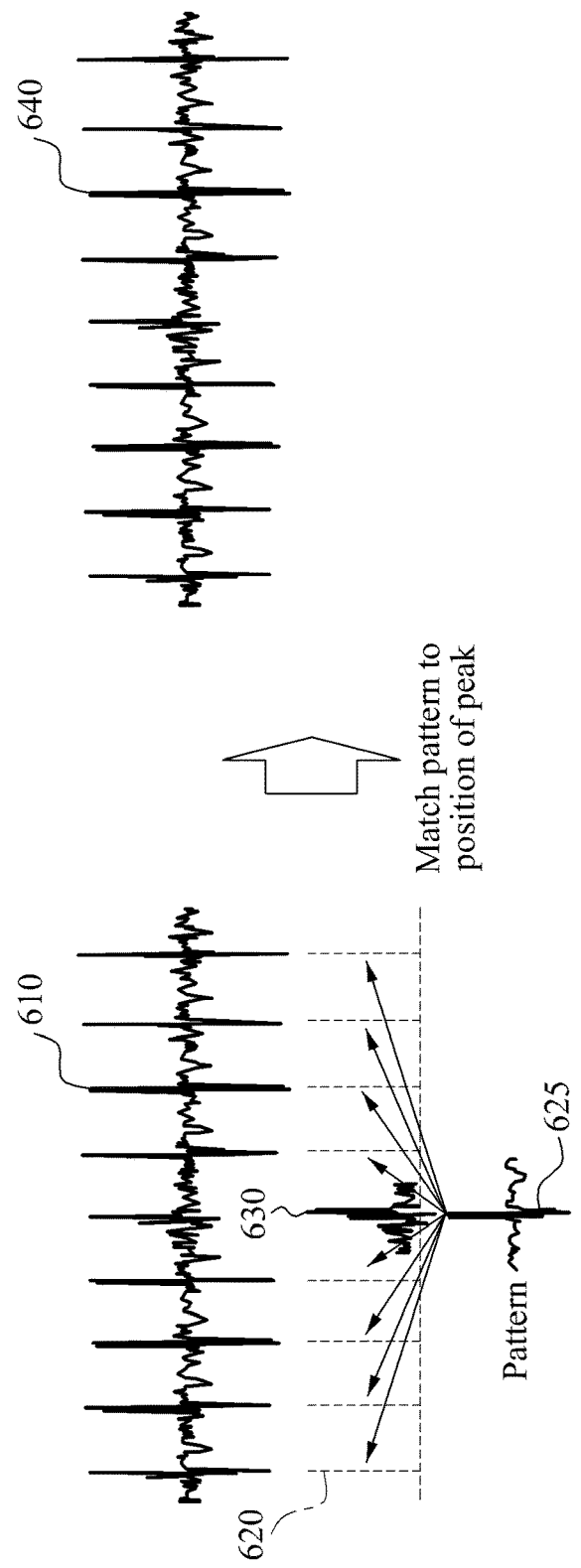

BIOSIGNAL TRANSMITTER, BIOSIGNAL RECEIVER, AND METHOD OF TRANSMITTING AND RECEIVING BIOSIGNAL

CROSS-REFERENCE TO RELATED APPLICATIONS

This application is a Divisional Application of U.S. application Ser. No. 14/056,705, filed Oct. 17, 2013, now U.S. Pat. No. 9,427,157, that claims the benefit under 35 USC 119(a) of Korean Patent Application No. 10-2012-0127417 filed on Nov. 12, 2012, in the Korean Intellectual Property Office, the disclosure of which is incorporated herein by reference in its entirety for all purposes.

BACKGROUND

1. Field

The following description relates to a biosignal transmitter, a biosignal receiver, a method of transmitting and receiving a biosignal, and technology for transmitting and receiving a biosignal based on a feature point included in the biosignal and a pattern related to the biosignal.

2. Description of Related Art

With an increasing level of interest in ubiquitous healthcare (U-healthcare), new technologies for monitoring and analyzing a vital signal in a daily life are being developed. Various applied technologies, for example, an electrocardiogram (ECG) measurement device using a fibrous electrode, a wrist band type or ring type heart rate detecting module, a chest band type or glove type heart rate detector, are being attempted.

Such devices may be provided in a wearable form, and thus should have super-light and super-small characteristics for a user's convenience.

SUMMARY

In one general aspect, a biosignal transmitter includes a biosignal obtaining unit configured to obtain a biosignal including a plurality of unit signals; a parsing unit configured to parse the biosignal to extract a first unit signal of the plurality of unit signals; a pattern obtaining unit configured to obtain a pattern related to the biosignal based on the first unit signal; and a transmitting unit configured to transmit information related to a feature point of the first unit signal based on the first unit signal and the pattern.

The parsing unit may be further configured to extract the first unit signal by detecting respective peaks of the plurality of unit signals, and parsing the biosignal based on positions of the peaks.

The pattern obtaining unit may include a determining unit configured to determine whether the pattern is generated based on the first unit signal; an obtaining unit configured to obtain the pattern in response to a determination that the pattern is generated; and a generating unit configured to generate the pattern in response to the determining unit determining that that the pattern is yet to be generated.

The determining unit may be further configured to obtain a first pattern stored in a storage space provided in advance; determine whether the first pattern corresponds to a waveform of the first unit signal; and determine that the pattern is generated in response to the determining unit determining that the first pattern corresponds to the waveform of the first unit signal; and the obtaining unit may be further configured to obtain the first pattern as the pattern.

The generating unit may be further configured to receive a predetermined number of unit signals from the parsing unit; and calculate an average of the predetermined number of the unit signals to generate the pattern.

The transmitting unit may be further configured to calculate a correlation between the first unit signal and the pattern; extract the feature point in response to the correlation being greater than or equal to a predetermined threshold value; and transmit the information related to the feature point.

The transmitting unit may be further configured to transmit the first unit signal in response to the correlation being lower than the predetermined threshold value.

The transmitting unit may be further configured to transmit the pattern in response to the pattern being newly generated by the pattern obtaining unit to obtain the pattern.

The information related to the feature point may include an amplitude and a position of a peak in the first unit signal.

The biosignal may have a periodicity, the plurality of unit signals may include the first unit signal and a second unit signal, and a waveform of the first unit signal and a waveform of the second unit signal may be classified as an identical pattern.

The biosignal may include an electrocardiogram (ECG), and the pattern may depend on a position of an electrode configured to measure the ECG.

In another general aspect, a biosignal receiver includes a receiving unit configured to receive a reception signal related to a biosignal including a plurality of unit signals; a determining unit configured to determine a type of the reception signal; a pattern obtaining unit configured to obtain a pattern related to the biosignal from a storage space provided in advance in response to the determining unit determining that the type of the reception signal is a first type of reception signal; and a unit signal reconstructing unit configured to reconstruct a first unit signal of the plurality of unit signals based on the pattern and information related to a feature point of the first unit, signal; and the reception signal determined to be the first type of reception signal may include the information related to the feature point of the first unit signal.

The biosignal receiver may further include a pattern storing unit configured to store the pattern related to the biosignal in the storage space in response to the determining unit determining that the type of the reception signal is a second type of reception signal; and the reception signal determined to be the second type of reception signal may include the pattern related to the biosignal.

The biosignal receiver may further include a unit signal obtaining unit configured to obtain a second unit signal of the plurality of unit signals in response to the determining unit determining that the type of the reception signal is a third type of reception signal; and the reception signal determined to be the third type of reception signal may include the second unit signal.

The biosignal receiver may further include a biosignal reconstructing unit configured to reconstruct the biosignal based on the first unit signal and the second unit signal.

In another general aspect, a biosignal transmitting method of transmitting a transmission signal related to a biosignal including a plurality of unit signals includes obtaining the biosignal; parsing the biosignal to extract a first unit signal of the plurality of unit signals; obtaining a pattern related to the biosignal based on the first unit signal; and transmitting information related to a feature point of the first unit signal based on the first unit signal and the pattern.

The obtaining of the pattern may include determining whether the pattern is generated; obtaining the pattern in response to a result of the determining being that the pattern is generated; and generating the pattern in response to a result of the determining being that the pattern is yet to be generated.

The transmitting may include calculating a correlation between the first unit signal and the pattern; and extracting the feature point in response to the correlation being greater than or equal to a predetermined threshold value.

The transmitting may include transmitting the first unit signal in response to the correlation being lower than the predetermined threshold value; and transmitting the pattern in response to the pattern being newly generated to obtain the pattern in the obtaining of the pattern.

In another general aspect, a non-transitory computer-readable storage medium stores a program for controlling a computer to perform the method described above.

In another general aspect, a biosignal receiving method of receiving a reception signal related to a biosignal including a plurality of unit signals includes receiving the reception signal; determining a type of the reception signal; obtaining a pattern related to the biosignal from a storage space provided in advance in response to a result of the determining being that the type of the reception signal is a first type of reception signal; and reconstructing a first unit signal of the plurality of unit signals based on the pattern and information related to a feature point of the first unit signal; and the reception signal determined to be the first type of reception signal may include the information related to the feature point of the first unit signal.

The method may further include storing the pattern related to the biosignal in the storage space in response to a result of the determining being that the type of the reception signal is a second type of reception signal; and obtaining a second unit signal of the plurality of unit signals in response to a result of the determining being that the type of the reception signal is a third type of reception signal; the reception signal determined to be the second type of reception signal may include the pattern related to the biosignal; and the reception signal determined to be the third type of reception signal may include the second unit signal.

The method may further include reconstructing the biosignal based on the first unit signal and the second unit signal.

In another general aspect, a biosignal transmitting method includes extracting a signal from a biosignal; obtaining a biosignal pattern based on the signal; determining a similarity between the signal and the biosignal pattern; obtaining information related to the signal based on the signal and the biosignal pattern and transmitting the information related to the signal in response to the similarity being greater than a predetermined threshold; and transmitting the signal in response to the similarity being less than the predetermined threshold.

The transmitting of the information related to the signal may require transmitting a smaller amount of data than the transmitting of the signal.

The obtaining of the biosignal pattern may include determining whether the signal corresponds to a predetermined biosignal pattern; obtaining the predetermined biosignal pattern as the obtained biosignal pattern in response to a result of the determining being that the signal corresponds to the predetermined biosignal pattern; and generating a new biosignal pattern as the obtained biosignal pattern in response to a result of the determining being that the signal does not correspond to the predetermined biosignal pattern; and the method may further include transmitting the new biosignal pattern.

Other features and aspects will be apparent from the following detailed description, the drawings, and the claims.

BRIEF DESCRIPTION OF THE DRAWINGS

FIGS. 2A and 2B are diagrams illustrating an example of an operation of a parsing unit.

FIG. 6 is a diagram illustrating an example of an operation of a biosignal receiver.

DETAILED DESCRIPTION

Figure 1:
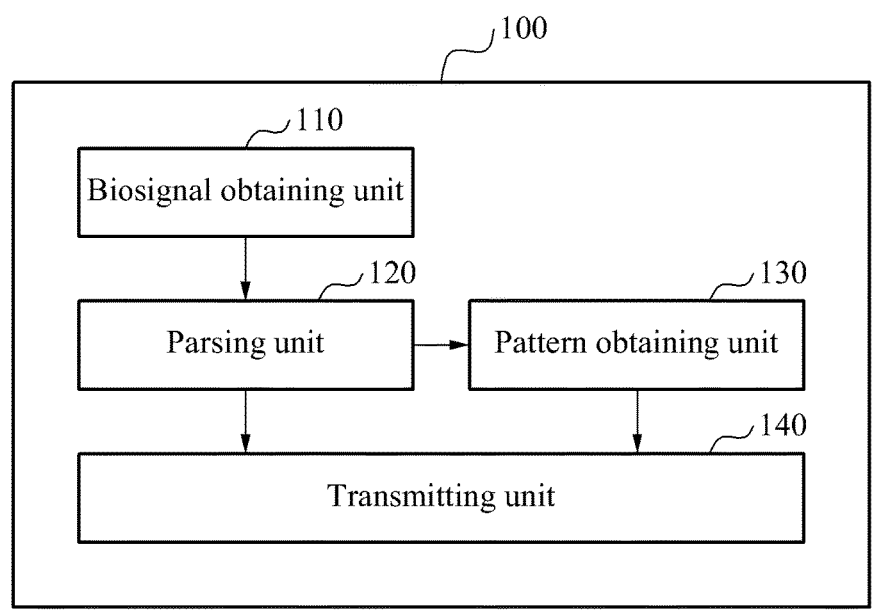
FIG. 1 is a block diagram illustrating an example of a biosignal transmitter.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a block diagram illustrating an example of a biosignal transmitter 100. Referring to FIG. 1, the biosignal transmitter 100 includes a biosignal obtaining unit 110, a parsing unit 120, a pattern obtaining unit 130, and a transmitting unit 140.

The biosignal obtaining unit 110 obtains a biosignal including a plurality of unit signals. The biosignal may be a signal having a periodicity, and may include, for example, an electrocardiogram (ECG), or other signal having a periodicity. The biosignal may include a signal having a predetermined pattern repeated periodically. For example, the biosignal may include a first unit signal and a second unit signal. A waveform of the first unit signal and a waveform of the second unit signal may be classified as an identical pattern.

The biosignal obtaining unit 110 may obtain the biosignal using various schemes. For example, the biosignal obtaining unit 110 may measure a biosignal using a sensor included in the biosignal transmitter 100. Also, the biosignal obtaining unit 110 may obtain a biosignal by receiving a sensing result measured by a sensor positioned remotely in a wired or wireless manner.

The parsing unit 120 parses the biosignal to extract the first unit signal included in the plurality of unit signals. The parsing unit 120 may parse the biosignal based on a period of the biosignal, thereby extracting the plurality of unit signals. The parsing unit 120 may calculate information related to the period of the biosignal based on respective peaks included in the plurality of unit signals. An operation of the parsing unit 120 will be described in detail below with reference to FIGS. 2A and 2B.

The pattern obtaining unit 130 obtains a pattern related to the biosignal based on the first unit signal extracted by the parsing unit 120. Hereinafter, the pattern related to the biosignal will be referred to as the "biosignal pattern."

The pattern obtaining unit 130 may determine whether a pattern corresponding to the waveform of the first unit signal is generated. The pattern obtaining unit 130 may retrieve the corresponding pattern from a storage space provided in advance when it is determined that the pattern corresponding to the waveform of the first unit signal is generated.

The pattern obtaining unit 130 may newly generate the pattern corresponding to the waveform of the first unit signal when it is determined that the pattern corresponding to the waveform of the first unit signal is yet to be generated. The pattern obtaining unit 130 may generate the pattern corresponding to the waveform of the first unit signal based on the first unit signal and a predetermined number of unit signals, for example, 8 unit signals.

The pattern obtaining unit 130 may obtain the pattern corresponding to the waveform of the first unit signal extracted by the parsing unit 120. An operation of the pattern obtaining unit 130 will be described in detail below with reference to FIGS. 3A and 3B.

The transmitting unit 140 transmits information related to a feature point of the first unit signal based on the first unit signal and the pattern.

The transmitting unit 140 may extract and transmit only the feature point of the first unit signal, instead of transmitting the entire first unit signal. For example, the transmitting unit 140 may detect a peak included in the first unit signal, and may transmit an amplitude of the detected peak, and a position of the detected peak, for example, a temporal position of the detected peak. The biosignal transmitter 100 may provide technology for reducing a number of data bits to be used for transmitting the bio biosignal based on quasi-periodic and deterministic characteristics of the biosignal.

Accordingly, the biosignal transmitter 100 may reduce an amount of power to be consumed for transmitting the biosignal. An operation of the transmitting unit 140 will be described in detail below with reference to FIGS. 4A and 4B.

A pattern of a biosignal may differ on an individual basis, and may also differ based on a position of an electrode for measuring the biosignal. The biosignal transmitter 100 may provide technology for generating a personalized biosignal pattern, and transmitting only a feature point of a biosignal using the generated biosignal pattern. A biosignal receiver may reconstruct a biosignal using a biosignal pattern and a feature point. The biosignal receiver will be described in detail below with reference to FIGS. 5 and 6.

Figure 2A:
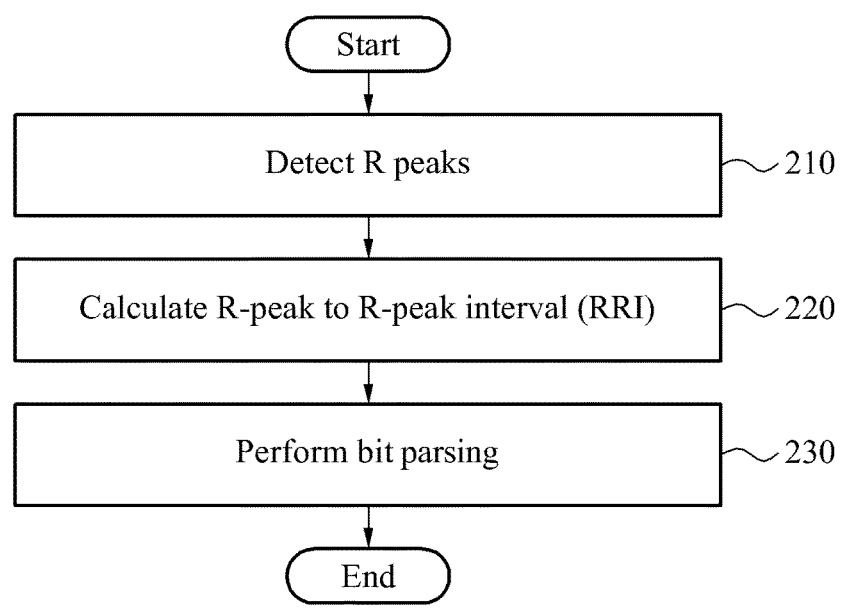

FIGS. 2A and 2B are diagrams illustrating an example of an operation of a parsing unit. Referring to FIG. 2A, the parsing unit parses a biosignal to extract a first unit signal included in a plurality of unit signals.

The parsing unit may extract the first unit signal by detecting respective peaks of the plurality of unit signals and parsing the biosignal based on positions of the detected peaks.

For example, the biosignal may correspond to an ECG waveform 205 as shown in FIG. 2B. The ECG waveform 205 may be a quasi-periodic signal having a repeating pattern of a periodic PQRST waveform.

In 210, the parsing unit detects respective R peaks 215 of a plurality of unit signals included in the ECG waveform 205. The parsing unit may detect the R peaks 215 through various preprocessing processes. The parsing unit may employ preprocessing processes known to one of ordinary skill in the art, such as a low-pass filter (LPF), a high-pass filter (HPF), a comb filter, a differentiator, and a squaring circuit.

In 220, the parsing unit calculates a distance between adjacent R peaks, for example, an R-peak to R-peak interval (RRI). The parsing unit may extract an amplitude and a position of the R peak 215. The position of the R peak 215 may refer to a temporal position of the R peak 215, and may include a position on an X axis in the graphs of FIG. 2B. The parsing unit may calculate the RRI by calculating a difference between a position of the R peak 215 and a position of a previous R peak on the X axis.

In 230, the parsing unit extracts a first unit signal 235 by parsing the ECG waveform 205 based on the calculated RRI. The parsing unit may extract the first unit signal 235 by performing beat parsing in a −RRI/2 to a +RRI/2 area based on the R peak 215.

Figure 3A:
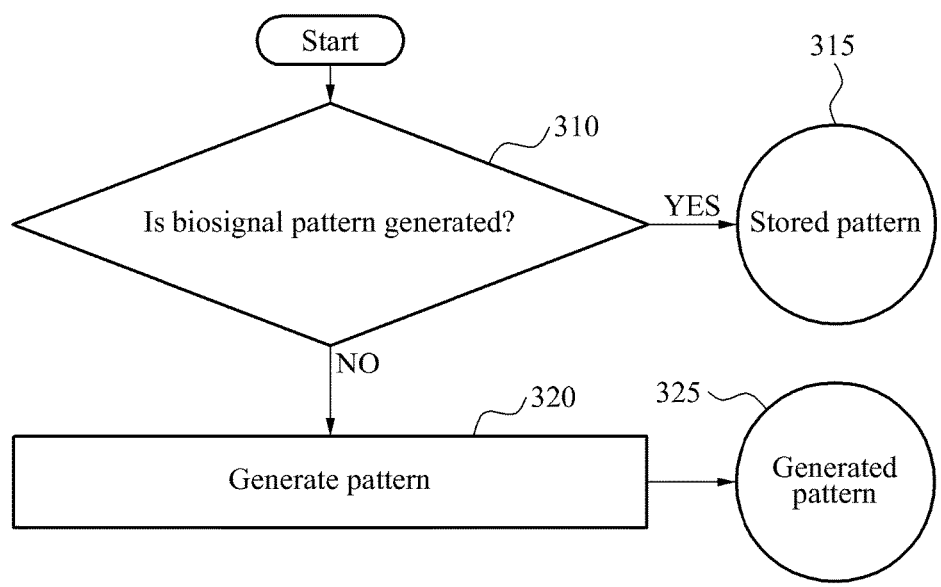
FIGS. 3A and 3B are diagrams illustrating an example of an operation of a pattern obtaining unit.
Figure 3B:
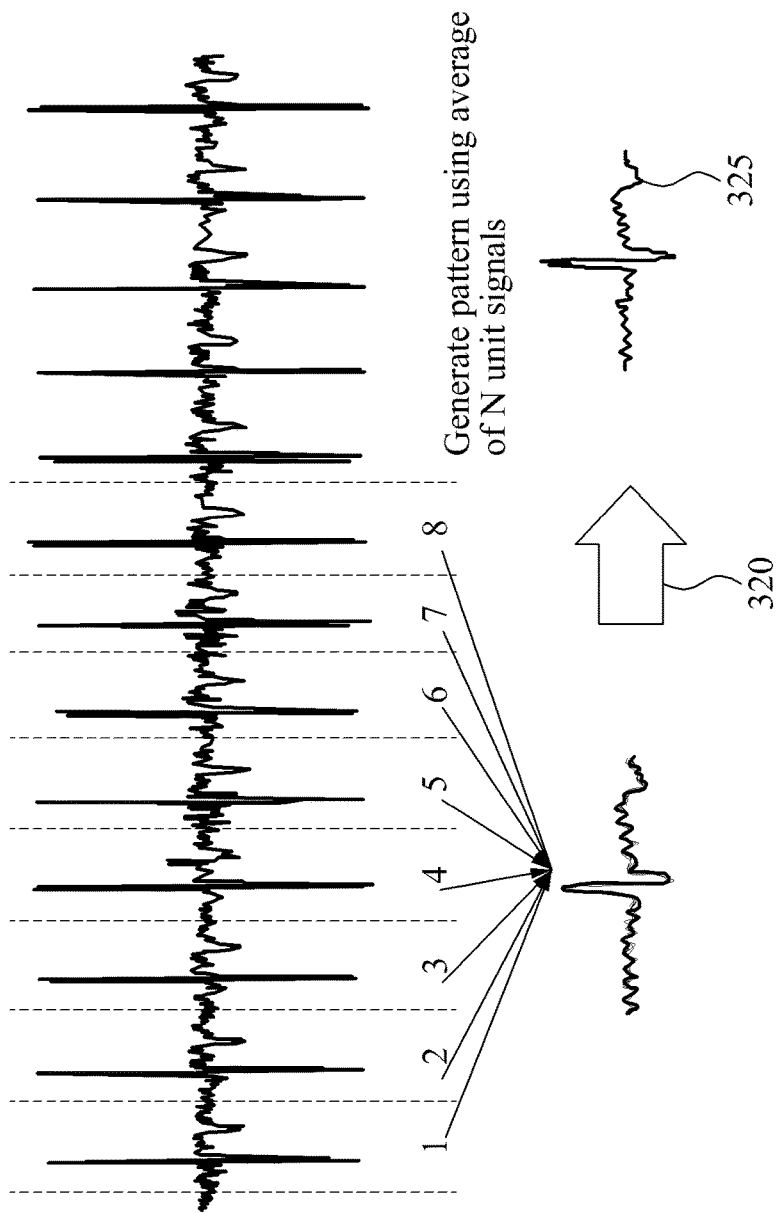

FIGS. 3A and 3B are diagrams illustrating an example of an operation of a pattern obtaining unit. Referring to FIG. 3A, the pattern obtaining unit may obtain a biosignal pattern based on a first unit signal.

In 310, the pattern obtaining unit determines whether the biosignal pattern is generated based on the first unit signal. For example, the pattern obtaining unit may obtain a first pattern stored in a storage space provided in advance, and may determine whether the first pattern corresponds to a waveform of the first unit signal.

When it is determined that the first pattern corresponds to the waveform of the first unit signal, the pattern obtaining unit may determine that the biosignal pattern is generated. The pattern obtaining unit may determine whether a waveform of a first unit signal currently being input is similar to a prestored first pattern, using a waveform comparing scheme, for example, correlation matching, or other matching scheme. When a correlation between the first unit signal and the first pattern is greater than or equal to a predetermined correlation threshold value, the pattern obtaining unit may determine that the first pattern corresponds to the waveform of the first unit signal, and may determine that the biosignal pattern is generated.

When it is determined that the biosignal pattern is generated, the pattern obtaining unit may obtain a pre-generated biosignal pattern. When it is determined that the biosignal pattern is generated, the pattern obtaining unit may obtain a first pattern 315 stored in the provided storage space, as the biosignal pattern.

Conversely, when the first pattern fails to correspond to the waveform of the first unit signal, the pattern obtaining unit may determine that the biosignal pattern is yet to be generated. When the correlation between the first unit signal and the first pattern is lower than the predetermined correlation threshold value, the pattern obtaining unit may determine that the first pattern fails to correspond to the waveform of the first unit signal, and may determine that the biosignal pattern is yet to be generated.

A case in which the first pattern fails to correspond to the waveform of the first unit signal may include a case in which reconstructing the first unit signal using the first pattern is impossible. For example, when a user utilizing a biosignal transmitter is changed, or when a part for measuring a biosignal is changed, the prestored first pattern may fail to correspond to the waveform of the first unit signal being input.

In addition, when the first pattern is absent in the provided storage space, the pattern obtaining unit may determine that the biosignal pattern is yet to be generated. When the biosignal transmitter is used initially, the prestored first pattern may be absent.

In 320, the pattern obtaining unit generates the biosignal pattern when it is determined that the biosignal pattern is yet to be generated. Referring to FIG. 3B, the pattern obtaining unit may generate a biosignal pattern 325, by receiving, from a parsing unit, a predetermined number of unit signals, for example, 8 unit signals, and calculating an average of the received unit signals.

Respective waveforms of the predetermined number of the unit signals, for example, the 8 unit signals, may correspond to a normal beat pattern. The pattern obtaining unit may perform correlation matching with respect to the predetermined number of the unit signals, for example, the 8 unit signals, and may calculate the average of the unit signals when it is determined that waveforms of the unit signals are similar.

As another example, the pattern obtaining unit may sense that an input signal is stabilized. When it is sensed that the input signal is stabilized, the pattern obtaining unit may perform the operations described above. Accordingly, when the input signal is unstable, the pattern obtaining unit may prevent successive generation of biosignal patterns. For example, when an electrode for measuring a biosignal is attached improperly, although the biosignal transmitter is turned on, a pattern of the biosignal to be input for each period may be changed continuously. The pattern obtaining unit may perform an operation, for example, an operation of verifying whether a generated pattern is present, after the input signal is stabilized, thereby preventing generation of an unnecessary biosignal pattern.

As still another example, the pattern obtaining unit may be unresponsive to an input of an abnormal pattern, as opposed to a normal pattern, by sensing that the input signal is stabilized. The pattern obtaining unit may distinguish a case in which a biosignal pattern being input is changed due to a change of a user or a change in a position at which the biosignal is measured from a case in which the biosignal pattern is changed due to an occurrence of the abnormal pattern. In the case in which the biosignal pattern being input is changed due to the change of the user or the change in the position at which the biosignal is measured, the pattern obtaining unit may generate a new biosignal pattern. Conversely, when the biosignal pattern is changed due to the occurrence of the abnormal pattern, the pattern obtaining unit may not generate the new biosignal pattern.

Figure 4A:
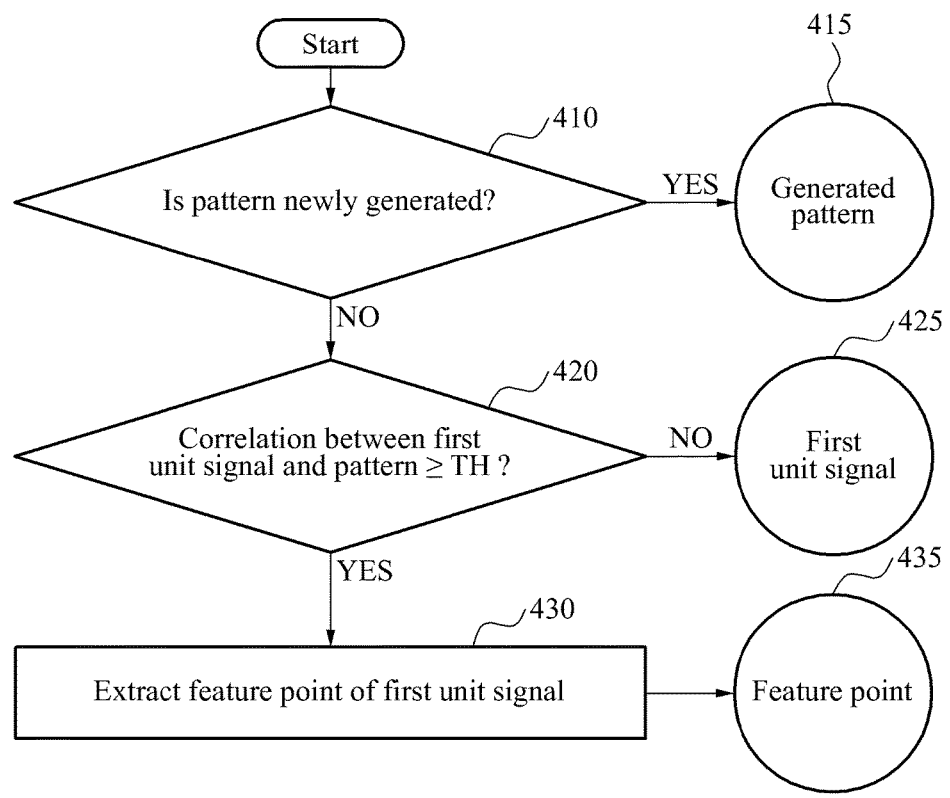
FIGS. 4A and 4B are diagrams illustrating an example of an operation of a transmitting unit.
Figure 4B:
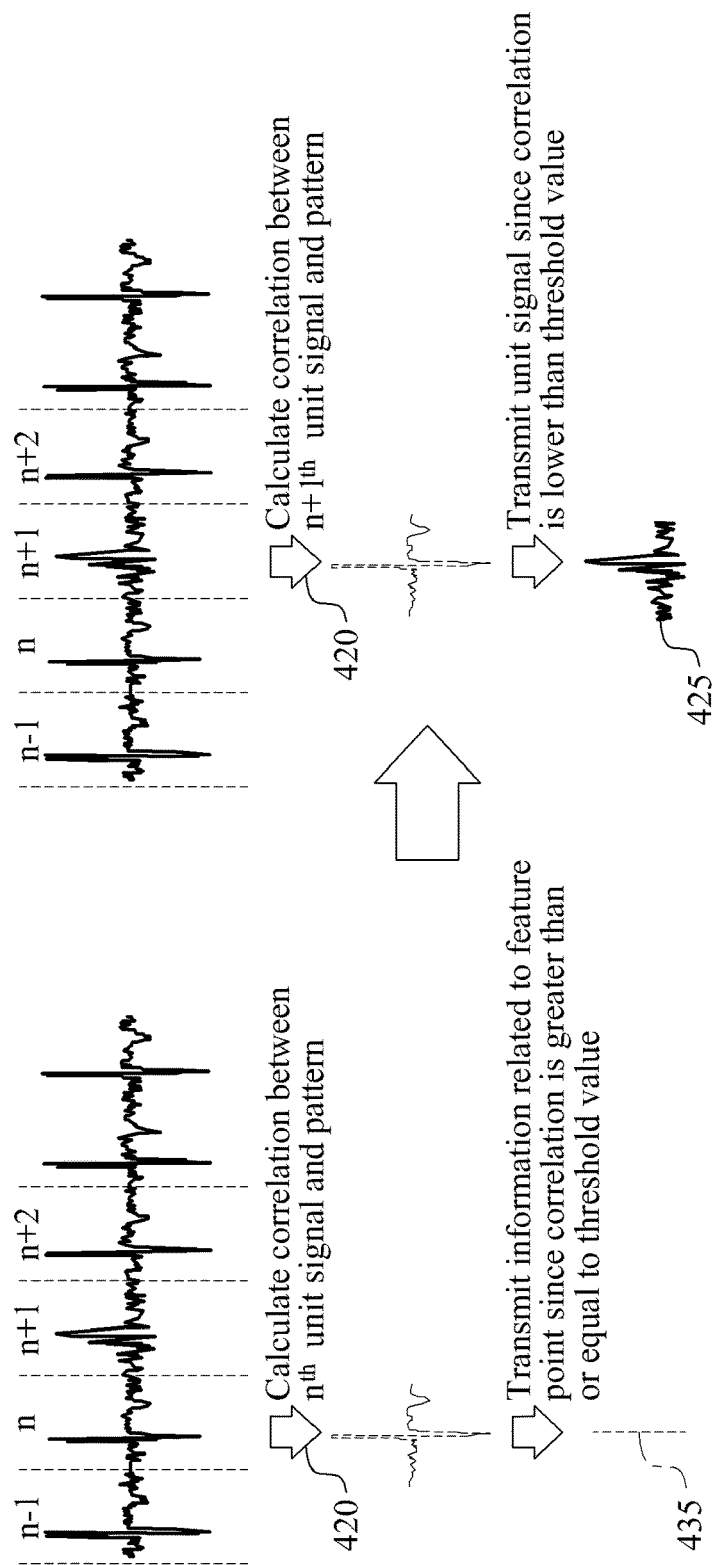

FIGS. 4A and 4B are diagrams illustrating an example of an operation of a transmitting unit. Referring to FIG. 4A, in 410, the transmitting unit determines whether a biosignal pattern is newly generated by a pattern obtaining unit. When it is determined that the biosignal pattern is newly generated by the pattern obtaining unit, the transmitting unit may transmit the newly generated biosignal pattern 415.

In 420, the transmitting unit calculates a correlation between a first unit signal extracted by a parsing unit and the biosignal pattern obtained by the pattern obtaining unit, and determines whether the calculated correlation is greater than or equal to a predetermined threshold value, for example, 0.9.

When it is determined that the calculated correlation is lower than the predetermined threshold value, for example, 0.9, the transmitting unit may transmit a first unit signal 425. For example, when an abnormal pattern, as opposed to a normal pattern, is sensed, the transmitting unit may transmit the abnormal pattern. In a case of a patient having a heart disease, an abnormal heart disease pattern, for example, an arrhythmia pattern, may occur. In this case, the transmitting unit may transmit the heart disease abnormal pattern when the abnormal heart disease pattern occurs. When an abnormal pattern is sensed, the transmitting unit may transmit the abnormal pattern, rather than extracting a feature point of the abnormal pattern, thereby increasing an accuracy of the measured biosignal.

Conversely, when it is determined that the calculated correlation is greater than or equal to the predetermined threshold value, for example, 0.9, the transmitting unit extracts a feature point of the first unit signal in 430. The transmitting unit may transmit information related to the extracted feature point 435. The case in which the correlation between the first unit signal and the biosignal pattern is greater than or equal to the predetermined threshold value, for example, 0.9, may include a case in which reconstructing the first unit signal using the biosignal pattern and the feature point is possible.

The information related to the feature point 435 may include an amplitude and a position of a peak included in the first unit signal. The transmitting unit may extract the peak of the first unit signal, and may extract an amplitude and a position of the extracted peak as the information related to the feature point 435. For example, when the biosignal corresponds to an ECG waveform, the transmitting unit may extract an R peak of the first unit signal, and may transmit an amplitude and a position of the extracted R peak. Accordingly, when a normal pattern is sensed, the transmitting unit may transmit only the information related to the feature point 435, thereby reducing a number of bits to be used for transmitting the biosignal, and reducing an amount of power to be consumed for transmitting the biosignal.

Figure 5:
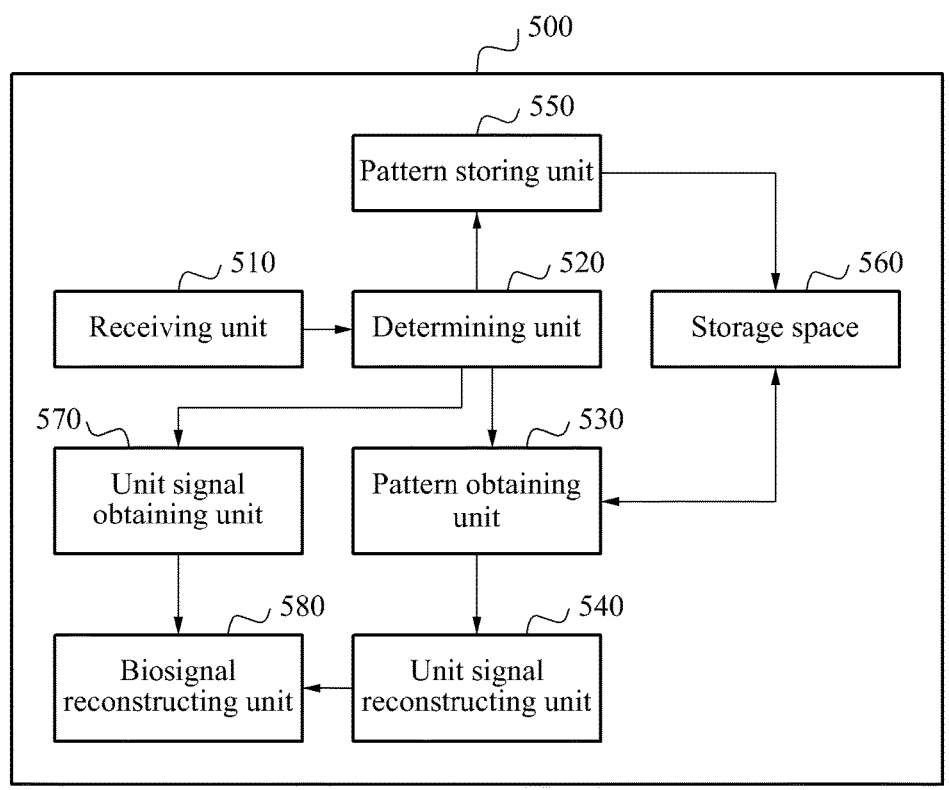
FIG. 5 is a block diagram illustrating an example of a biosignal receiver.

FIG. 5 is a block diagram illustrating an example of a biosignal receiver 500. Referring to FIG. 5, the biosignal receiver 500 includes a receiving unit 510, a determining unit 520, a pattern obtaining unit 530, and a unit signal reconstructing unit 540.

The receiving unit 510 receives a reception signal related to a biosignal including a plurality of unit signals. The determining unit 520 determines a type of the reception signal.

The type of the reception signal may include any one or any combination of a first type, a second type, and a third type. A reception signal of the first type may include information related to a feature point of a first unit signal included in the plurality of unit signals. A reception signal of the second type may include a biosignal pattern. A reception signal of the third type may include a second unit signal included in the plurality of unit signals.

When a feature point is extracted by a biosignal transmitter, a signal of the first type may be transmitted. When a biosignal pattern is newly generated by the biosignal transmitter, a signal of the second type may be transmitted. When an abnormal pattern is sensed by the biosignal transmitter, a signal of the third type may be transmitted.

The pattern obtaining unit 530 obtains a biosignal pattern from a storage space 560 provided in advance when the determining unit 520 determines that the type of the reception signal corresponds to the first type. In this example, the unit signal reconstructing unit 540 reconstructs the first unit signal based on the biosignal pattern and the information related to the feature point of the first unit signal.

For example, the information related to the feature point of the first unit signal may include an amplitude and a position of an R peak included in the first unit signal. The unit signal reconstructing unit 540 may reconstruct the first unit signal by matching an R peak of the biosignal pattern to the position of the R peak, and adjusting an amplitude of the biosignal pattern based on the amplitude of the R peak.

The biosignal receiver 500 further includes a pattern storing unit 550. The pattern storing unit 550 stores the biosignal pattern in the provided storage space 560 when the determining unit 520 determines that the type of the reception signal corresponds to the second type.

The biosignal receiver 500 further includes a unit signal obtaining unit 570. The unit signal obtaining unit 570 obtains the second unit signal from the determining unit 520 when the determining unit 520 determines that the type of the reception signal corresponds to the third type. The second unit signal may include an abnormal pattern sensed by the biosignal transmitter.

The biosignal receiver 500 further includes a biosignal reconstructing unit 580. The biosignal reconstructing unit 580 reconstructs the biosignal based on the first unit signal reconstructed by the unit signal reconstructing unit 540 and the second unit signal obtained by the unit signal obtaining unit 570.

FIG. 6 is a diagram illustrating an example of an operation of a biosignal receiver. Referring to FIG. 6, a biosignal transmitter transmits a signal 620 of a first type, a signal 625 of a second type, and a signal 630 of a third type based on a biosignal 610.

The biosignal receiver performs an operation of reconstructing a biosignal based on a type of a reception signal. The biosignal receiver may store a biosignal pattern in a storage space provided in advance when it is determined that the reception signal corresponds to the signal 625 of the second type including the biosignal pattern.

In addition, the biosignal receiver reconstructs a first unit signal using information related to a feature point of the first unit signal and the biosignal pattern stored in the provided storage space when it is determined that the reception signal corresponds to the signal 620 of the first type including the information related to the feature point of the first unit signal. The signal 620 of the first type may include an amplitude and a position of an R peak included in the first unit signal. As described above with reference to FIG. 5, the biosignal receiver may reconstruct the first unit signal by adjusting an amplitude and a position of the biosignal pattern using the amplitude and the position of the R peak.

Further, the biosignal receiver obtains a second unit signal when it is determined that the reception signal corresponds to the signal 630 of the third type including the second unit signal. The biosignal receiver may reconstruct a biosignal 640 using the first unit signal and the second unit signal. For example, the biosignal receiver may reconstruct the biosignal 640 by connecting the first unit signal with the second unit signal based on a position of the first unit signal and a position of the second unit signal.

Referring to Table 1 below, the biosignal transmitter may definitely reduce a number of data bits to be used for transmitting a biosignal. The biosignal to be transferred may be an ECG waveform, a sampling rate of the ECG waveform may be 250 hertz (Hz), and a single sample may consist of 2 bytes.

A size of a biosignal pattern may be changed based on a heart rate per minute. However, when it is assumed that the heart rate per minute is 60 beats per minute (beats/min), the size of the biosignal pattern may be 500 bytes. When the heart rate per minute corresponds to 60 beats/min, the heart may beat once per second. With the sampling rate of 250 Hz, the biosignal transmitter may perform data sampling 250 times for a single heart beat. Since the single sample consists of 2 bytes, the size of the biosignal pattern may be 500 bytes.

In addition, an amplitude and a position of an R peak corresponding to information related to a feature point may consist of 3 bytes.

TABLE 1

| TX time | Original signal | Pattern (HR = 60) | Pattern to original signal ratio | Pattern (HR = 60) + Abnormal waveform (Probability of 10%) | Pattern to original signal ratio |
|---|---|---|---|---|---|
| 1 sec | 500 Bytes | 500 Bytes | 100% | 500 Bytes | 100% |
| 1 min | 30 kBytes | 680 Bytes = 500 + 60 * 3 | 2.26% | 5.6 kBytes = 500 + 50*3 + 10*500 | 18.7% |
| 1 hr | 1.8 MBytes | 11.3 kBytes = 500 + 3600 * 3 | 0.62% | 190 kBytes = 500 + 3240*3 + 360*500 | 10.5% |
| 24 hrs | 43.2 MBytes | 259.7 kBytes = 500 + 86400*3 | 0.60% | 4.5 MBytes = 500 + 77760*3 + 8640*500 | 10.4% |

The three columns on the left side of Table 1 indicate a pattern to original signal ratio for a case in which only information related to a feature point is transmitted due to an abnormal pattern being undetected. It may be verified that the pattern to original signal ratio decreases below 1% as a transmission time increases.

Further, the three columns on the right side of Table 1 may indicate a pattern to original signal ratio for a case in which an abnormal pattern is detected with a probability of 10%. It may be verified that the pattern to original signal ratio converges to 10% corresponding to the probability with which the abnormal pattern is detected.

The biosignal transmitter and the biosignal receiver may be applied to a ubiquitous healthcare (U-healthcare) service. Hereinafter, it may be assumed that an ECG waveform corresponding to a representative of a heart function signal may be transmitted. However, it will be apparent to one of ordinary skill in the art that the identical scheme may be applied to a pulse wave, a photoplethysmography (PPG) signal, and other biosignals.

A user of the U-health service may measure a variety of health information by wearing a wearable terminal. The wearable terminal may transmit the measured health information to a server through a gateway terminal at home, or a wireless gateway terminal, for example, a cellular phone or other device capable of operating as a wireless gateway terminal. The server may store the received health information, and may provide a health information service for the user to retrieve and analyze the health information in real time or in an off-line manner.

The biosignal transmitter may be provided in a wearable form, and may have super-light and super-small characteristics for a user's convenience. The biosignal transmitter may generate a personalized pattern of an ECG waveform repeated periodically, and may transmit the generated pattern and a beat feature point of the ECG signal for each individual, thereby reducing an amount of power to be consumed for transmitting the ECG waveform. Accordingly, the biosignal transmitter may provide technology satisfying such super-light and super-small characteristics within a limited battery capacity.

The biosignal transmitter 100, the biosignal obtaining unit 110, the parsing unit 120, the pattern obtaining unit 130, and the transmitting unit 140 illustrated in FIG. 1 that perform the operations illustrated in FIGS. 2A, 2B, 3A, 3B, 4A, and 4B and the biosignal receiver 500, the receiving unit 510, the determining unit 520, the pattern obtaining unit 530, the unit signal reconstructing unit 540, the pattern storing unit 550, the storage space 560, the unit signal obtaining unit 570, and the biosignal reconstructing unit 580 illustrated in FIG. 5 that perform the operations illustrated in FIG. 6 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMS, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal receiver comprising:
one or more processors configured to:
determine a type of a received reception signal related to a biosignal comprising a plurality of unit signals;
obtain a pattern related to the biosignal from a storage space provided in advance in response to the type of the reception signal being determined to be a first type of reception signal; and
reconstruct a first unit signal of the plurality of unit signals based on the pattern and information related to a feature point of the first unit signal;
store the pattern related to the biosignal in the storage space in response to the type of the reception signal being determined to be a second type of reception signal; and
obtain a second unit signal of the plurality of unit signals in response to the type of the reception signal being determined to be a third type of reception signal,
wherein the reception signal determined to be the first type of reception signal comprises the information related to the feature point of the first unit signal,
wherein the reception signal determined to be the second type of reception signal comprises the pattern related to the biosignal, and
wherein the reception signal determined to be the third type of reception signal comprises the second unit signal.

2. The biosignal receiver of claim 1, wherein the one or more processors are further configured to reconstruct the biosignal based on the first unit signal and the second unit signal.

3. A processor-implemented method of transmitting a biosignal, the method comprising:
extracting a signal from the biosignal;
obtaining a biosignal pattern based on the signal, wherein the obtaining of the biosignal pattern further comprises:
obtaining the biosignal pattern in response to a determination that a correspondable pattern has previously been generated, and
obtaining signals from the biosignal and generating a pattern that correlates to the signal based on the obtained signals, in response to a determination that the correspondable pattern has not previously been generated;
transmitting the generated pattern in response to the pattern being newly generated;
determining a similarity between the signal and the biosignal pattern when the biosignal pattern is obtained, in the obtaining, without the generating of the pattern;
obtaining information related to at least one feature point of the signal based on the signal and the biosignal pattern and transmitting the information related to the at least one feature point of the signal, in response to the similarity being greater than a predetermined threshold; and
transmitting the signal, in response to the similarity being less than the predetermined threshold.

4. The method of claim 3, wherein the transmitting of the information related to the signal requires transmitting a smaller amount of data than the transmitting of the signal.

5. The method of claim 3, wherein the obtaining of the biosignal pattern comprises:
determining whether the signal corresponds to a predetermined biosignal pattern;
obtaining the predetermined biosignal pattern as the obtained biosignal pattern in response to a result of the determining being that the signal corresponds to the predetermined biosignal pattern; and
generating a new biosignal pattern as the obtained biosignal pattern in response to a result of the determining being that the signal does not correspond to the predetermined biosignal pattern; and
the method further comprises transmitting the new biosignal pattern.

6. A non-transitory computer-readable storage medium storing a program for controlling a computer to perform the method of claim 3.

7. A processor-implemented method of receiving a biosignal, the method comprising:
receiving a reception signal related to the biosignal comprising a plurality of unit signals;
determining a type of the reception signal;
obtaining a pattern related to the biosignal from a storage space provided in advance in response to the determining of the type of the reception signal determining that the reception signal is a first type of reception signal;
reconstructing a first unit signal of the plurality of unit signals based on the pattern and information related to a feature point of the first unit signal;
storing the pattern related to the biosignal in the storage space in response to the determining of the type of the reception signal determining that the reception signal is a second type of reception signal; and
obtaining a second unit signal of the plurality of unit signals in response to the determining of the type of the reception signal determining that the reception signal is a third type of reception signal,
wherein the reception signal determined to be the first type of reception signal comprises the information related to the feature point of the first unit signal,
wherein the reception signal determined to be the second type of reception signal comprises the pattern related to the biosignal, and
wherein the reception signal determined to be the third type of reception signal comprises the second unit signal.

8. A non-transitory computer-readable storage medium storing a program for controlling a computer to perform the method of claim 7.

9. A processor-implemented method of transmitting a biosignal, the method comprising:

obtaining the biosignal comprising a plurality of unit signals;

parsing the biosignal to extract a first unit signal of the plurality of unit signals;

generating a pattern that correlates to the first unit signal in response to a determining of which pattern, of a plurality of patterns, correlates to the first unit signal indicating that a correspondable pattern has not yet been generated;

transmitting the generated pattern that correlates to the first unit signal when the determining of which pattern correlates to the first unit signal indicates that the correspondable pattern has not yet been generated;

transmitting information related to a feature point of the first unit signal when the first unit signal correlates to a predetermined pattern; and transmitting the first unit signal when the first unit signal does not correlate to the predetermined pattern.

* * * * *